United States Patent

O'Brien

[11] Patent Number: 6,007,332
[45] Date of Patent: Dec. 28, 1999

[54] TOOTH COLOR MATCHING SYSTEM

[76] Inventor: William J. O'Brien, 1320 Morningside, Ann Arbor, Mich. 48103

[21] Appl. No.: 08/721,266

[22] Filed: Sep. 26, 1996

[51] Int. Cl.[6] .................................................. A61C 19/10
[52] U.S. Cl. ............................ 433/26; 43/203.1; 356/404
[58] Field of Search ........................... 433/26, 29, 203.1,
433/215; 365/413.28; 356/402, 405, 406, 408, 404

[56] References Cited

U.S. PATENT DOCUMENTS

| | | | |
|---|---|---|---|
| 3,436,157 | 4/1969 | Adler et al. | 356/192 |
| 3,507,042 | 4/1970 | Hana . | |
| 3,778,541 | 12/1973 | Bowker | 178/5.2 R |
| 3,878,384 | 4/1975 | Bowker | 235/151.3 |
| 3,986,777 | 10/1976 | Roll | 356/176 |
| 4,608,015 | 8/1986 | Smigel | 433/26 |
| 4,654,794 | 3/1987 | O'Brien | 364/413 |
| 4,813,000 | 3/1989 | Wyman et al. | 364/526 |
| 4,836,674 | 6/1989 | Lequime et al. | 433/26 |
| 5,055,040 | 10/1991 | Clar | 433/26 |
| 5,177,694 | 1/1993 | Graham et al. | 364/526 |
| 5,240,414 | 8/1993 | Thompson | 433/26 |
| 5,309,257 | 5/1994 | Bonino et al. | 358/504 |
| 5,313,291 | 5/1994 | Appel et al. | 358/501 |
| 5,317,425 | 5/1994 | Spence et al. | 358/504 |
| 5,383,020 | 1/1995 | Vieellefosse | 356/405 |

FOREIGN PATENT DOCUMENTS

| | | | |
|---|---|---|---|
| 4301530 | 10/1992 | Japan | 356/402 |
| 4338465 | 11/1992 | Japan | 433/203.1 |
| 1750676 | 7/1992 | U.S.S.R. | 433/26 |
| 8603292 | 6/1986 | WIPO | 433/203.1 |
| 9002929 | 3/1990 | WIPO | 433/203.1 |
| 9102955 | 3/1991 | WIPO | 433/203.1 |

*Primary Examiner*—Cary E. O'Connor
*Attorney, Agent, or Firm*—Rohm & Monsanto, P.L.C.

[57] ABSTRACT

A method and system for determining the color characteristic of a tooth, particularly in a mouth in which restorative dentistry is contemplated, employs the photographic imaging of the tooth of the patient, and the photographing of visually selected color standards, to achieve the final selection of the closest color match. The resulting photographic images, which may be on a single photograph, are subjected to calorimetric or spectrophotometric analysis to achieve the final selection of the closest match. The system avoids the need to rely upon the visual color acuity of the practitioner in order to achieve a close color match for a prosthetic device. Additionally, the method and system of the invention avoid the problems associated with color shifts associated with photography, when such is used alone as the indicator of tooth color.

24 Claims, 2 Drawing Sheets

TOOTH COLOR MATCHING SYSTEM

BACKGROUND OF THE INVENTION

1. Field of the Invention

This invention relates generally to dentistry, and more particularly, to a system of matching dental color for facilitating and improving restorative dental procedures.

2. Description of the Related Art

The prior art provides essentially three methods for determining the colors of teeth in dentistry. These include, visual matching against shade guide color standards, colorimetry, and photography. Visual matching systems that employ shade guide color standards constitute the predominant color matching system. With this known system, a practitioner visually matches the color of the patient's tooth that will be restored against a series of color standards. It is a significant problem with this known method that its success depends upon the color vision of the practitioner. In the practice of the known method, the practitioner first selects, by visual inspection, standard colors that exhibit, to his or her eye, a general match to the subject's tooth. Then, a final match is performed that requires excellent color matching ability on the part of the practitioner.

As intimated, this known method is flawed, as the quality of the resulting restoration is largely related to the skill of the particular practitioner, and his or her ability to detect small color differences in the final matching from among the closest color standards. In a study by Kuehi & Marcus (Color Res. Appl 4: 83–91, 1979), large differences in the ability to discriminate color was shown among plural subjects, such ability ranging from 0.5 to 6 CIE $\Delta E$ units. These measurements are determined using the known CIE L*a*b* system described, for example, in Bilmeyer, F. W., *Principles of Color Technology*, 2nd ed., John Wiley, 1981.

The prior art has sought to overcome some of the problems associated with visual color matching systems by applying colorimetry technology to the measurement of tooth colors in the clinic. However, this effort has not achieved success. A colorimeter was marketed in the 1970's (Chromoscan from Stemdent, N.Y.), but the unit failed to achieve adequate color discrimination (O'Brien & Nelsen, J. Prosthet. Dent. 49: 63–66, 1989). A more recent effort to overcome the stated problems is described in U.S. Pat. No. 4,654,794 ("O'Brien"), and employs a spectrophotometer. However, the prototype results were disappointing.

There are two major technical obstacles to successful clinical implementation of calorimeters to the measurement of tooth colors. First, the measurement of the color of translucent objects, specifically including teeth, suffers from inaccuracies that result from so-called "edge effects." As light from the calorimeter enters the tooth for measurement, it is scattered sideways away from the edges of the light beam. This results in significant diminution in the magnitude of light signal that is returned to the sensor. The second problem relates to the application of the calorimeter probe to the surface of the teeth, since teeth are irregular in shape. Colorimeters are designed to achieve accuracy of color measurement on flat, opaque objects.

Finally, photography has been used to show the color of teeth in lectures and textbooks, but it is known to be extremely inaccurate in reproducing color. During the several stages of the photographic process, uncorrectable color shifts take place which render accurate and reliable color reproduction not to be feasible. Nevertheless, practitioners regularly send photographs of patients' teeth to dental laboratories to show the approximate color.

It is, therefore, an object of this invention to provide a system for accurately determining the color of the teeth of a dental patient, without complete color discrimination reliance on the practitioner.

It is another object of this invention to provide a method producing a reliable record of color difference between the teeth of a dental patient and a color standard.

It is also an object of this invention to provide a method of selecting from a plurality of color standards, a color standard corresponding to the closest color match to the tooth of a dental patient;

It is a further object of this invention to provide a method of selecting from a plurality of color standards, each having a respectively associated color parameter, a one of the color standards corresponding to the closest color parameter match to the tooth of a dental patient;

It is additionally an object of this invention to provide a method of selecting from a plurality of color standards, each having a respectively associated color characteristic, a one of the color standards corresponding to the closest color parameter match to the corresponding color characteristic of a test subject.

It is yet a further object of this invention to provide a system for determining the color composition of a tooth whereby a restoration material can be formulated in response thereto.

It is also another object of this invention to provide a method of estimating the color parameters of a tooth of a dental patient.

SUMMARY OF THE INVENTION

The foregoing and other objects are achieved by this invention which provides a method of selecting a color standard color characteristic for a tooth prosthesis that closely matches the color characteristic of a selected original tooth. In accordance with the invention, the method includes the steps of:

1. selecting a plurality of color standards, each having a predetermined color characteristic that is determined visually to approximate the corresponding color characteristic of the original tooth;
2. photographing the original tooth and the plurality of color standards selected in the step of selecting;
3. tooth measuring the predetermined color parameter of the original tooth from a photograph produced in the step of photographing to produce a tooth color parameter value;
4. standards measuring the predetermined color parameter of each of at least two of the color standards from a photograph produced in the step of photographing to produce respective standards color parameter values; and
5. calculating respective values corresponding to the differences between the tooth color parameter value and the respective standards color parameter values, whereby the color standard associated with the smaller difference represents the closer color characteristic match to the color characteristic of the original tooth.

In a preferred embodiment of the invention, the determination of the color parameters of the dental patient's tooth is based upon the measured shift in color of a standard in the same photograph by the photographic process. The shift function of the standard in the photograph is used with an algorithm to calculate the original color parameters of the patient's tooth.

In one embodiment of the invention, the step of photographing includes the production of a plurality of photographs representing respective color characteristics of the original tooth and the color standards selected in the step of selecting. The photographic images may be in the form of color print, transparency, or monochrome print.

In accordance with a further method aspect of the invention there is provided a method of matching the color characteristic of a tooth with a plurality of color standards, the method comprising the steps of:

1. inspecting visually the tooth and the plurality of the color standards;
2. selecting from the plurality of the color standards a number of the color standards that are determined in the step of inspecting visually to approximate the color characteristic of the tooth;
3. photographing the tooth and the number of the color standards selected in the step of inspecting visually;
4. employing a selectable one of a calorimeter and a spectrophotometer to measure a color parameter of the images obtained in the step of photographing of the tooth and of the selected color standards; and
5. determining the one of the selected color standards that is associated with the photographic image of the selected color standards having the minimum color difference from the tooth as determined by the measurement of the step of employing.

In a preferred embodiment of this further method aspect of the invention, the determination of the color parameters of the dental patient's tooth is based upon the measured shift in color of a standard in the same photograph by the photographic process. Again, the shift function of the standard in the photograph is used with an algorithm to calculate the original color parameters of the patient's tooth.

In a specific illustrative embodiment of the further method aspect of the invention, a photograph is produced in the step of photographing is a color print. As previously noted, the photograph may be any of a color print, a transparency, or a monochrome print.

In accordance with a system aspect of the invention, there is provided a system for determining a color characteristic of a tooth. The system is provided with a plurality of color standards, each for establishing a predetermined respective color parameter. A photographic apparatus produces a photographic tooth image of the tooth and respective photographic color standard images of selected ones of the plurality of color standards. In some embodiments, the tooth and the color standard images are imaged in one photograph. An arrangement for measuring a predetermined color parameter of the photographic tooth image is provided to produce a tooth image signal responsive thereto and for measuring a corresponding predetermined color parameter of each of the photographic color standard images of the selected ones of the plurality of color standard means, and further to produce respective color standard image signals corresponding to respectively associated ones of the selected ones of the plurality of color standard means. There is additionally provided an arrangement for comparing the tooth image signal to each of the color standard image signals.

In a specific illustrative embodiment of the system aspect of the invention, the arrangement for measuring photographic image color parameters is a colorimeter. In other embodiments, it is a spectrophotometer. The photographic apparatus includes a camera. The camera may have, in respective embodiments, a color film, a monochromatic film; a transparency film, or any other suitable image recording medium installed therein. Alternatively, the camera may be of the instant development-type, such as a Polaroid® camera. A lighting arrangement, as will be described in detail below, is arranged in certain embodiments to cooperate with the photographic equipment, and produces a predetermined light which may have a determined color character, illustratively as a result of translucent filtering. Also as will be described below, the plurality of color standards are each provided with an aperture for facilitating viewing of the tooth therethrough. The arrangement for comparing the tooth image signal to each of the color standard image signals includes, in certain embodiments, a numerical display associated with the arrangement for measuring.

BRIEF DESCRIPTION OF THE DRAWING

Comprehension of the invention is facilitated by reading the following detailed description in conjunction with the annexed drawings, in which.

DETAILED DESCRIPTION

Figure 1:
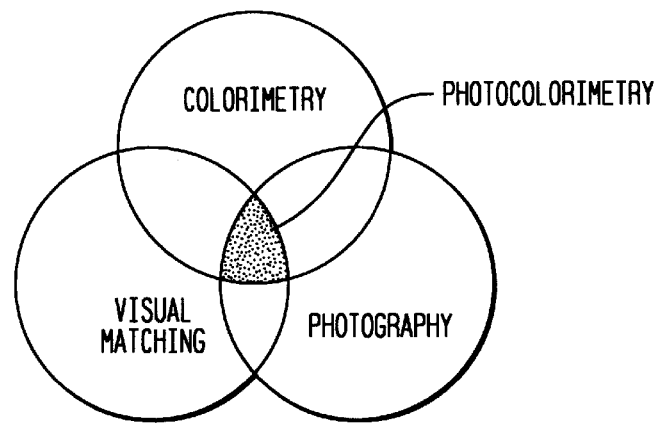
FIG. 1 is a diagram that is useful to illustrate the technological disciplines incorporated in the present invention.

FIG. 1 is a diagram that is useful to illustrate the technological disciplines incorporated in the present invention. As stated hereinabove, the present invention constitutes a hybrid system of photocolorimetry that combines visual, photographic, and calorimetric approaches to form a system of matching the color of teeth.

Figure 2:
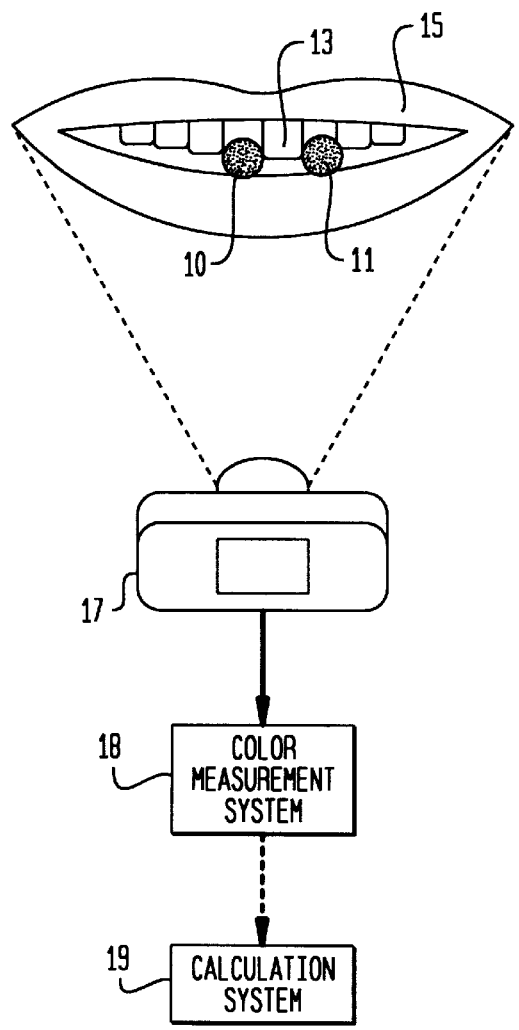
FIG. 2 is a schematic representation of an arrangement for photographing the tooth of a dental patient and a pair of color standards simultaneously, and further illustrating schematically arrangements for measuring color parameters and calculating a photographic shift function.

FIG. 2 is a schematic representation of an arrangement for photographing the tooth of a dental patient and a pair of color standards simultaneously. The method of the present invention involves, in a first aspect thereof, three steps. First, as shown in FIG. 2, a practitioner (not shown) uses a plurality of color standards and selects therefrom the two or three closest matches to the patient's teeth, preferably under color corrected or balanced light sources. FIG. 2 shows first and second color standards, 10 and 11, respectively, arranged adjacent to a tooth 13 of a dental patient 15. Next, the practitioner photographs with a camera 17 the patient's tooth 13, and the previously selected color standards 10 and 11. These items can be photographed individually. However, it is preferred that the standards be photographed together with the teeth, as shown in the specific illustrative embodiment of FIG. 2, since each photograph will be characterized by a unique color shift. As will be discussed in greater functional detail below, the output of camera 17, which will be in the form of a photographic image (not shown) of tooth 13 and standards 10 and 11, is subjected to a color measurement system 18 where a color shift spectrum (not shown) for the process by which the photographic images were formed is determined, by reference to the known spectrum of a color standard. The output of the color measurement system is directed to a calculation system 19 that will calculate the color spectrum of the tooth, combine same with, in this specific illustrative embodiment of the invention, information related to a CIE standard source and CIE color-matching functions for equal energy spectra, to determine CIE color parameters, as described hereinbelow.

Figure 3:
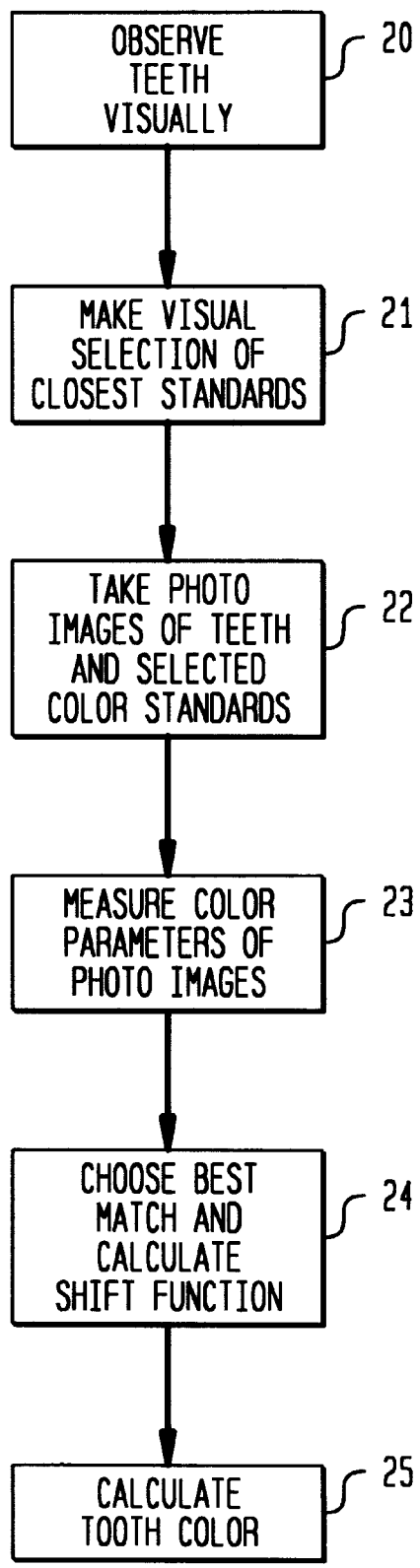
FIG. 3 is a function block diagram that illustrates, in simplified form, the major steps of the inventive process.

FIG. 3 is a function block diagram that illustrates, in simplified form, the major steps of the inventive process.

Function block 20 sets forth the observation of the tooth of the dental patient (not shown in this figure), as described above. The practitioner (not shown) then observes visually at function block 21 the color standards and makes a preliminary selection of the ones thereof that appear closest to the color of the patient's tooth. At function block 22, the practitioner photographs the tooth of the patient simultaneously with the visually selected color standards, as described above with respect to FIG. 2.

The practitioner then, at function block 23 of FIG. 3 measures the color parameters of the photographic images of the teeth and color standards on the clinical photograph with a colorimeter in the known CIE L*a*b* or other color system. In a preferred embodiment, the match is determined by calculating, as set forth in function block 24, the color difference in accordance with the following relationship:

$$\Delta E^* = \sqrt{(\Delta L^*)^2 + (\Delta a^*)^2 + (\Delta b^*)^2}$$

wherein the closest color characteristic match between the patient's tooth and the color standards corresponds to the particular color standard, the image of which has associated therewith the minimum color value difference from the tooth image, as determined by the calorimeter.

The present invention is based in part on the discovery by the inventor herein that although the photographic process shifts the colors of teeth and of the color standards, relative color differences are preserved among color samples that are relatively close in color. It has also been found that subtractive color photography, or additive color photography with monochrome photography, may be employed in the practice of the invention. The calorimetric measurements on the photographs, as set forth herein, serve to substitute for the prior art's problematical final visual matching by the practitioner to select the closest of the color standards.

In addition to obviating the need for visual matching of the color of teeth to select the closest color standard, the present invention affords the additional advantage of providing a method for estimating the numerical color parameters of the teeth. These parameters are useful in formulating new materials when the color characteristic of the teeth does not match existing materials or the color characteristics of the color standards. In the practice of this additional advantage afforded by the present invention, the photographing color standards that have been determined visually to approximate the color characteristic of the teeth, as well as the teeth, is performed as previously described. However, a spectrophotometer (e.g., Color Eye, Macbeth, Inc.) is used to determine the spectral $R_o(\lambda)$ reflectance of the color standards and the photographic images of the standards and teeth from around 400 nm to around 700 nm. These data are used as follows in estimating the color parameters of the teeth:

First the color shift function of the photographic process is determined by dividing the spectral reflectance of the photographic image of the closest matching color standard, $R_{ps}(\lambda)$ by the spectral reflectance of the color standard, $R_{os}(\lambda)$ to give the shift function, $S_p(\lambda)$, $$\text{STANDARD } S_p(\lambda) = \frac{R_{ps}(\lambda)}{R_{os}(\lambda)}$$

This shift function is then used to estimate the color parameter of the tooth by dividing the spectral reflectance curve of the photographic image of the tooth by the shift function as follows:

$$\text{TOOTH } R_{OT}(\lambda) = \frac{R_{pt}(\lambda)}{S_p(\lambda)}$$

Once the calculated spectral response curve of the tooth is obtained, the calculation of CIE or other color parameters for a given standard light source and observer is routine and is known to persons of skill in the art of colorimetry.

DESCRIPTION OF THE PREFERRED EMBODIMENTS

In order to determine a color match for a patient's teeth using the photocolorimetric system, a number of photographic processes may be used in conjunction with visual matching and colorimetry. Photography that produces a negative from which color prints can be made provides an excellent photographic process. Instant color photography using Polaroid technology has the advantage of simplicity and speed in producing a print. Reversal color films which reproduce color by subtractive three-color synthesis with three layers may be used in the form of slides. Additive or trichromatic photography uses black and white panchromatic film with colored filters and is applicable to this present invention. Teeth are photographed along with tooth color standards with colored lens filters (e.g., red, blue, yellow, green, etc.) on black and white panchromatic film. CIE L* measurements are then made on the photographed tooth and color standard images with a calorimeter. The best matching color standard to the teeth will have the closest L* values in photographs made with the three filters, since this represents the lowest $\Delta E^*$ value for a black and white photograph with a* and b* values close to zero.

The control of incident lighting is an essential element in successful determination of tooth color matches with photocolorimetry. Generally, any photographic filter that will enhance the saturation of the low chroma teeth images will increase the accuracy of color measurements. The yellow and yellow-red colors of teeth and matching shade guides may be enhanced in photographs by the use of colored photographic filters placed over the lens of the camera or over the light source. For example, the yellow color of teeth was enhanced by placing a combination of 5Y and 2.5 magenta Wratten filters, available from Kodak, Inc., over the flash attachment of the camera. The filtered light reaching the teeth during photography is therefore slightly enriched in yellow-red which increases the saturation of the color of the photographic images. This increase in saturation results in an increase in the CIE b* values measured, which increases the ability to detect small color differences between the teeth and the color standards. In other situations, filters of a complementary color will better enhance color differences between the color standards and the teeth. Persons skilled in the field of photography can select appropriate filters for illumination based on general colors of the teeth to enhance color differences. In most situations, daylight or conventional Xenon strobe lights will function satisfactorily in the practice of the invention. In addition to the spectrum of the light, the intensity of the incident light must be uniform on the teeth and on the color standards. Otherwise, color differences between the photographed images of the teeth and color standards will result from the uneven lighting rather than from actual differences in surface reflectance spectra.

Uniform distribution of light is achieved in two ways. First, gloss which represents areas on the objects where there is high specular reflection from the light source, needs to be minimized. An effective method of minimizing gloss on areas of the object where color measurements will be made involves controlling the angle of incidence and the angle photographed. In this way, the site of the gloss may be directed away from the center of the tooth or other area where the color measurements of the photographic image will be made. For example, an incident light arranged at approximately between 45° and 75° with respect to the surface and above the mandibular central incisor teeth, with the camera lens perpendicular to the teeth, will direct the gloss area to the gingival third of the teeth.

The use of polarizing filters affords another method of reducing gloss. Still another important approach to obtaining uniform lighting of the teeth and of the color standards involves keeping the teeth and the color standards as close together as possible in space to the incident light source. In the practice of one such method, conventional shade guide color standards are placed adjacent to the teeth with incisal edge to incisal edge, rather than proximal surface to proximal surface, with the shade guide tooth over a natural tooth, as is commonly done. It is noted that achieving uniform lighting and avoiding gloss in critical areas of the teeth being photographed are within the capabilities of those having ordinary photographic skills and conventional equipment.

EXAMPLE 1

A tooth was selected for color matching with the Bioform Shade Guide (Dentsply International, Inc., York, Pa.). The tooth and Bioform Shade Guide color standards were illuminated with the Ney-Lite, which provides CIE Illuminant C (J. M. Ney Co., Hartford, Conn.). Three approximate color matches were selected visually (#59, #51, and #91) from the Bioform Shade Guide. Next, the tooth, along with the approximate shade matches, was photographed with a Nikon single lens reflex camera with Kodak Vericolor Type III professional film, taking care to avoid specular reflection in the center of the tooth and shade guide teeth. The film was then sent for C-41 processing to produce color negatives. Color prints were then made with RA chemistry and Fuji paper. Color measurements were then made on the photograph of the tooth and shade guide images in the CIE L*a*b* system and the color differences calculated between the tooth image parameters and those of the Bioform standards. The CIE ΔE* values between the 59, 51, and 91 standards and the tooth average were calculated with the formula:

$$\Delta E^* = \sqrt{(\Delta L^*)^2 + (\Delta a^*)^2 + (\Delta b^*)^2}$$

The values of ΔE were 1.58, 6.59, and 7.03, respectively. Therefore, Bioform shade #59 was selected as the closest shade to match for the tooth.

EXAMPLE 2

A tooth color was matched with three Munsell color standards visually under daylight. The tooth and the Munsell color standards (5Y 8/12, 5Y 8/6, and 5Y 8/4) were photographed with Kodak T-max 100 black and white film using a Nikon® F3 camera. Three photographs were made with green, red, and blue filters. The CIE L* values were measured of the tooth and Munsell color standard images on the black and white prints made from the processed negatives. The L* values found are given below:

| | L* Values | | |
|---|---|---|---|
| Subject | Green Filter | Red Filter | Blue Filter |
| Tooth | 81 | 86 | 54 |
| 5Y 8/12 | 76 | 86 | 22 |
| 5Y 8/6 | 80 | 87 | 54 |
| 5Y 8/4 | 80 | 86 | 67 |

The best match between the L* values of the Munsell color standards and the tooth color was for the 5Y 8/6 sample, which was chosen as the color match for the tooth.

EXAMPLE 3

This example illustrates a method of matching a tooth color against a bioform shade guide B91 standard. The tooth and the B91 standard were photographed together with Kodak® Vericolor Type III professional film with a Nikon® single lens reflex camera. The film was developed using C-41 processing, and a color print was obtained using C-41 processing and Fuji® paper. The reflectance spectrum of the B91 color standard, $R_o(\lambda)$, was measured along with the reflectance spectrum of the B91 photographic image, $R_p(\lambda)$, using a Macbeth Color Eye Spectrophotometer. In accordance with function block 24 of FIG. 3, the shift function, $S_p(\lambda)$, of the B91 color standard was calculated as follows:

$$S_p(\lambda) = \frac{R_p(\lambda)}{R_o(\lambda)}$$

using a computer for λ values between 400 and 700 mm. The reflectance spectrum for the tooth photographic image, $R_p(\lambda)$, was measured with the spectrophotometer. Then, in accordance with function block 25 of FIG. 3, the original tooth color spectrum, $R_o(\lambda)$, was then calculated with the relationship:

$$R_o(\lambda) = \frac{R_p(\lambda)}{S_p(\lambda)}$$

where $S_p(\lambda)$ is the shift function of the B91 standard. Once $R_o(\lambda)$ for the tooth was obtained, the CIE L*a*b* parameters were calculated using the Macbeth Color Eye spectrophotometer program. The CIE L*a*b* parameters obtained were 76, −0.42, 14, and 79, −1.0, 16 respectively, for the B91 standard and tooth.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof

What is claimed is:

1. A method of selecting a color standard color characteristic for a tooth prosthesis of a patient that matches closely the color characteristic of a selected original tooth, the method comprising the steps of:

selecting a plurality of color standards, each having a predetermined color characteristic that is determined visually to approximate the corresponding color characteristic of the original tooth;

photographing the original tooth and the plurality of color standards selected in said step of selecting;

tooth color measuring the predetermined color parameter of the original tooth from a photograph produced in said step of photographing to produce a tooth color parameter value;

standards color measuring the predetermined color parameter of each of at least two of the color standards from a photograph produced in said step of photographing to produce respective standards color parameter values; and calculating respective values corresponding to the differences between the tooth color parameter value and the respective standards color parameter values, whereby the color standard associated with the smaller difference represents the closer color characteristic match to the color characteristic of the original tooth.

2. The method of claim 1, wherein, in said step of photographing, there are produced a plurality of photographs representing respective color characteristics of the tooth and the color standards selected in said step of selecting.

3. The method of claim 1, wherein said photograph is a color print.

4. The method of claim 1, wherein said photograph is a transparency.

5. The method of claim 1, wherein said photograph is a monochrome print.

6. A method of matching the color characteristic of a tooth with a plurality of color standards, the method comprising the steps of:

inspecting visually the tooth and the plurality of the color standards;

selecting from the plurality of the color standards a number of the color standards that are determined in said step of inspecting visually to approximate the color characteristic of the tooth;

photographing the tooth and the number of the color standards selected in said step of inspecting visually;

employing a selectable one of a colorimeter and a spectrophotometer to measure a color parameter of the images obtained in said step of photographing of the tooth and of the selected color standards; and determining the one of the selected color standards that is associated with the photographic image of the selected color standards having the minimum color difference from the tooth as determined by the measurement of said step of employing.

7. The method of claim 7, wherein a photograph produced in said step of photographing is a color print.

8. The method of claim 7, wherein a photograph produced in said step of photographing is a monochrome print.

9. The method of claim 7, wherein a photograph produced in said step of photographing is a transparency.

10. A system for determining a color characteristic of a tooth, the system comprising:

a plurality of color standard means, each for establishing a predetermined respective color parameter;

photographic means for producing a photographic tooth image of the tooth and respective photographic color standard images of selected ones of said plurality of color standard means;

means for measuring a predetermined color parameter of said photographic tooth image to produce a tooth image signal responsive thereto and for measuring a corresponding predetermined color parameter of each of said photographic color standard images of said selected ones of said plurality of color standard means to produce respective color standard image signals corresponding to respectively associated ones of said selected ones of said plurality of color standard means; and means for comparing said tooth image signal to each of said color standard image signals.

11. The system of claim 10, wherein said means for measuring comprises a colorimeter.

12. The system of claim 10, wherein said means for measuring comprises a spectrophotometer.

13. The system of claim 10, wherein said photographic means comprises a camera.

14. The system of claim 13, wherein said photographic means further comprises a color film for said camera.

15. The system of claim 13, wherein said photographic means further comprises a monochromatic film for said camera.

16. The system of claim 13, wherein said photographic means further comprises a transparency film for said camera.

17. The system of claim 10, wherein said photographic means comprises an instant development-type camera.

18. The system of claim 10, wherein there is further provided lighting means for producing a predetermined light.

19. The system of claim 10, wherein said plurality of color standard means are each provided with an aperture for facilitating viewing of the tooth therethrough.

20. The system of claim 10, wherein said means for comparing comprises a numerical display associated with said means for measuring.

21. A system for determining a color parameter of a tooth, the system comprising:

a plurality of color standards, each for establishing a predetermined respective color parameter;

photographic means for producing a photographic tooth image of the tooth and a respective photographic color standard image of a selected one of the color standards;

measuring means for measuring the spectra of the photographic tooth image and at least one of the photographic color standard images; and calculating means for calculating the color parameter of the tooth.

22. The system of claim 21, wherein said measuring means comprises a spectrophotometer.

23. The system of claim 21, wherein said measuring means is arranged to calculate a color shift function characteristic of said photographic means.

24. The system of claim 23, wherein said calculating means is arranged to determine the color parameter of the tooth in response to the color shift function characteristic of said photographic means.

* * * * *